(12) United States Patent
Kroll et al.

(10) Patent No.: US 7,162,299 B1
(45) Date of Patent: Jan. 9, 2007

(54) ICD WITH VF PREVENTION

(75) Inventors: Mark W. Kroll, Simi Valley, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 692 days.

(21) Appl. No.: 10/163,591

(22) Filed: Jun. 5, 2002

(51) Int. Cl.
*A61N 1/39* (2006.01)

(52) U.S. Cl. ............................................. 607/14

(58) Field of Classification Search ................ 607/4, 607/5, 14, 9; 600/515, 516, 518
See application file for complete search history.

(56) References Cited

U.S. PATENT DOCUMENTS

| | | | |
|---|---|---|---|
| 3,939,844 A * | 2/1976 | Pequignot ................... | 607/14 |
| 4,403,614 A | 9/1983 | Engle et al. ................ | 128/419 |
| 4,493,325 A * | 1/1985 | Hartlaub et al. ............. | 607/14 |
| 4,941,471 A | 7/1990 | Mehra ........................ | 128/419 |
| 5,243,978 A | 9/1993 | Duffin, Jr. .................. | 607/11 |
| 5,301,677 A * | 4/1994 | Hsung ........................ | 600/518 |
| 5,312,451 A | 5/1994 | Limousin et al. ............ | 607/15 |
| 5,466,254 A | 11/1995 | Helland ...................... | 607/123 |
| 5,545,182 A * | 8/1996 | Stotts et al. ................. | 607/5 |
| 5,683,424 A | 11/1997 | Brown et al. ................ | 607/5 |
| 5,713,367 A | 2/1998 | Arnold et al. ............... | 128/704 |
| 5,792,193 A | 8/1998 | Stoop ......................... | 607/14 |
| 5,842,997 A | 12/1998 | Verrier et al. ............... | 600/518 |
| 5,855,592 A * | 1/1999 | McGee et al. ............... | 607/4 |
| 5,991,659 A | 11/1999 | De Vries et al. ............. | 607/9 |
| 6,035,233 A | 3/2000 | Schroeppel et al. ......... | 600/515 |
| 6,049,735 A | 4/2000 | Hartley et al. .............. | 607/9 |
| 6,058,328 A | 5/2000 | Levine et al. ............... | 607/14 |
| 6,078,836 A | 6/2000 | Bouhour et al. ............. | 607/14 |
| 6,115,627 A | 9/2000 | Street ......................... | 600/515 |
| 6,169,919 B1 | 1/2001 | Nearing et al. ............. | 600/518 |
| 6,169,923 B1 * | 1/2001 | Kroll .......................... | 607/5 |
| 6,216,038 B1 * | 4/2001 | Hartlaub et al. ............. | 607/31 |
| 6,272,377 B1 | 8/2001 | Sweeney et al. ............ | 600/515 |
| 6,308,094 B1 | 10/2001 | Shusterman et al. ........ | 600/516 |
| RE37,480 E | 12/2001 | Denker ....................... | 607/14 |
| 6,400,982 B1 * | 6/2002 | Sweeney et al. ............ | 600/515 |
| 6,490,478 B1 * | 12/2002 | Zhang et al. ............... | 600/518 |
| 6,636,765 B1 * | 10/2003 | Amely-Velez ................ | 607/9 |
| 6,678,547 B1 * | 1/2004 | Carlson et al. ............. | 600/515 |
| 6,735,472 B1 * | 5/2004 | Helland ....................... | 607/5 |

OTHER PUBLICATIONS

Taylor, E., M.D. et al., "Analysis of the Pattern of Initiation of Sustained Ventricular Arrhythmias in Patients with Implantable Defibrillators," Journal of Cardiovasular Electrophysiology, vol. 11, No. 7, Jul. 2000.

Leclercq, J.F. et al., "Respective Role of Sympathetic Tone and of Cardiac Pauses in the Genesis of 62 Cases of Ventricular Fibrillation Recorded During Holter Monitoring," European Heart Journal (1988) 9, 1276-1283.

U.S. Appl. No. 09/457,277, Pianca et al., "A Self Anchoring, Steerable Coronary Sinus Lead," filed Dec. 8, 1999.

* cited by examiner

*Primary Examiner*—George R. Evanisko
*Assistant Examiner*—Terri Lynn Smith

(57) ABSTRACT

A cardiac stimulation device includes a sensing unit for monitoring the electrical activity of a heart and a controller configured to predict the onset of an arrhythmia of the heart. The controller calculates a statistical indicia relating to the immediate past four R—R intervals in the form of a sliding average thereof. Upon the prediction that the risk of the onset of an arrhythmia is high, the controller compares the current value of the R—R interval to the indicia. If the current value of the R—R interval exceeds the indicia by a predetermined amount, the controller causes a high amplitude pacing pulse to be delivered to a selected cardiac site in an attempt to forestall the initiation of ventricular fibrillation.

38 Claims, 3 Drawing Sheets

ICD WITH VF PREVENTION

FIELD OF THE INVENTION

The present invention is directed to a method and device for predicting the onset of an arrhythmia of the heart and applying remedial relatively high amplitude pacing pulses to selected cardiac sites to forestall the initiation of ventricular fibrillation.

BACKGROUND OF THE INVENTION

Implantable medical devices such as pacemakers and cardioverter defibrillators are configured to monitor the electrical activity in various chambers of a patient's heart. In doing so, the devices can assess whether cardiac activity is consistent with desired cardiac function or whether abnormalities, such as arrhythmias, are present. The devices are usually programmed to deliver remedial therapy, typically in the form of the selective delivery of cardiac stimulation pulses, for bradycardia pacing, antitachycardia pacing, cardioversion and defibrillation therapy.

As is recognized in the field, the initiation of remedial treatment solely based upon the detection of arrhythmias, such as tachycardia and fibrillation, requires considerable preparation time and sometimes places the patient at risk due to the severity of the cardiac condition just prior to the initiation of therapy. This is particularly true for conditions involving ventricular tachyarrhythmias and fibrillation. Without rapid remedial response to ventricular tachyarrhythmias and fibrillation, the likelihood of patient death is relatively high. The mechanisms for developing appropriate remedial cardiac stimulation pulses require finite and often lengthy time periods. Obviously, the greater the time required to monitor cardiac activity and deliver therapy, the greater the potential for patient injury and death.

Implantable cardiac stimulation devices that maintain a constant monitor of cardiac activity for the purposes of predicting the onset of a cardiac arrhythmia provides a "first alert" so as to place the stimulation device at the "ready" to deliver therapy. Preferably and advantageously, providing therapy prior to the onset of an arrhythmia would not only put less strain and demand on the stimulation device but would also maintain the patient in the least traumatized state. As a further consideration, it would be advantageous to provide a second test to confirm the necessity of delivering therapy once a prediction of arrhythmia has been made so as to avoid response to "false positives".

Accordingly, an implantable medical device configured to predict the onset of cardiac arrhythmia, while utilizing a confirmatory test to trigger delivery of therapy would be most preferable. In such case, therapy would then be provided with the highest confidence of necessity.

SUMMARY OF THE INVENTION

This invention is directed to the detection and analysis of cardiac activity patterns predictive of the initiation of chronic ventricular arrhythmias. Upon such detection the invention further provides the delivery of selected cardiac stimulation pulses intended to prevent the initiation and persistence of ventricular arrhythmias. According to a preferred embodiment, once the prediction is made that the risk of ventricular fibrillation is high, a comparison is made to compare a current cardiac activity parameter to an indicia representative of the immediate past cardiac activity. A high amplitude cardiac pacing pulse is delivered to a selected cardiac site when the difference between the current cardiac activity parameter and the indicia exceeds a pre-selected threshold value.

As is recognized in the field of cardiac rhythm management, maintained ventricular arrhythmias derive from selected electrophysiological abnormalities. Polymorphic ventricular tachycardia (PMVT) is known to derive from ischemia, electrolyte imbalance and abnormalities of repolarization and commonly results from functional re-entry or triggered activity. In terms of triggered activity, patients with "torsades de pointes" due to QT prolongation are predisposed to ventricular arrhythmias.

In the case of sustained monomorphic VT, the more common occurrence of tachycardia is in patients with a history of myocardial infarction usually initiated by a late coupled ventricular depolarization. In cases of ventricular tachycardia, there exists a period of time after which the VT transforms into life endangering ventricular fibrillation (VF). For polymorphic VT that time on the average is 40 seconds and for monomorphic VT that time is on the average about 80 seconds. The onset of ventricular arrhythmias of differing mechanisms has been discovered to be preceded by distinct initiation sequences in cardiac activity. The transformation of VT into VF is related to three factors namely: the VT duration and rate and typically the widening of the QRS complex.

Three characteristics of the initiation of VT or VF that may be compared with preceding events are the variation of the coupling interval of the extrasystole; the R—R interval immediately preceding it and the morphology of the ventricular extrasystole initiating the VT. As is understood, a significant percentage of the episodes of VF are initiated by a long pause followed by a premature ventricular contraction (PVC) which occurs earlier with respect to the next expected conducted ventricular depolarization. Under strict conditions, that is, without first establishing that the risk of VF is high, remedial action may otherwise be taken even if an aberrant event such as a single extended R—R interval occurs in an otherwise normally occurring set of R—R intervals. This single event may generate a "false positive" that would otherwise be ignored.

To forestall delivering any remedial therapy (prior to entering any comparison or evaluation phase), the method of an embodiment of the present invention, first determines whether the risk of VF is high, if yes, then the method begins to calculate a measure of performance such as for example, a sliding average of the immediate past four R—R intervals. If the instantaneous R—R interval exceeds a pre-selected percentage of the average then selected cardiac rhythm management therapy is applied. Typically the therapy applied is the delivery of a high magnitude pacing pulse to provoke a heartbeat before the PVC can be developed. In such case, the potential of the PVC occurring is minimized, if not eliminated, and the possibility of the PVC initiating a VF is minimized, if not eliminated.

To establish one criterion for determining the potential of the onset of VF based upon cardiac activity, a "pause" is defined as an R—R interval exceeding the average cycle length of a predetermined number of preceding cardiac beats. Preferably, the number of preceding beats may be in the range of from 3 to 8 beats. Obviously fewer beats may be used however in such case, the statistical reliability of the calculated average may be compromised. Whereas, a greater number of beats used to calculate an average cycle length, while providing a greater statistical reliability may result in approaching the onset of VT/VF long before a remedial ventricular stimulation pulse is delivered. As will be described in detail later, the application of a remedial stimulation pulse to other cardiac sites is contemplated by the present invention.

Preferably a sliding average of the last four R—R intervals is calculated by the microcontroller. Although monitoring specific cardiac indicia as an indication of the desirability to deliver pre-emptive ventricular stimulation pulses to forestall VT and VF, a possibility nevertheless exists that an aberrant "false positive" may trigger the delivery of a stimulation pulse prematurely. In such case, a stimulation pulse will be delivered to an otherwise normally functioning heart. Preferably to prevent such occurrence, the present invention contemplates monitoring the VF prognostics and if it is determined that after such monitoring that the risk of VF is relatively "high", then the microcontroller will initiate the delivery of a ventricular stimulation pulse when the preselected criterion for delivering a stimulation pulse is met.

Techniques for predicting cardiac arrhythmias to establish the risk of the onset of VF are applicable to the present invention. For example, a method for predicting the onset of life threatening cardiac arrhythmias (LTCA) based upon the intervals between heart beats (R—R series) and the pattern of changes in these intervals, i.e., R—R variability, is described in U.S. Pat. No. 6,308,094 to Shusterman et al., incorporated herein by reference. A Karkunen-Loeve Transform (KLT) is used to characterize a patient's R—R interval series which involves the use of linear and non-linear changes in the R—R series as VF prognostics to predict the onset of LTCA.

A second method for predicting the onset of LTCA, extracts data representative of the QRS complex and calculates its power spectrum which is repeated for successive heartbeats. A calculation of the energy fractions in the spectrum that falls within various frequency bands is made as well as the variance of such changes over successive QRS complexes. A change, such as a decrease in the variance, presages the onset of an arrhythmia. This technique is described in detail in U.S. Pat. No. 6,115,627 to Street which is incorporated herein by reference.

A still further VF prognostics technique is described in U.S. Pat. No. 5,842,997 to Verrier et al., which is incorporated herein by reference. Verrier describes analysis of the morphology of an ECG, the use of T-wave alternans and QT interval dispersion as well as heart rate variability as predictors of cardiac electrical stability. With regard to T-wave alternans, which is considered to be an excellent predictor of cardiac instability, the location of the T-wave in each heart beat of the ECG is estimated and portioned into segments. The sampled ECG signal in each segment is summed together and a time series is formed for each segment that includes corresponding segments from successive T-waves. A dynamic estimation utilizing for example, a technique called complex demodulation is performed on each series to estimate the alternation for each segment. The amplitude of the alteration is a measure of cardiac susceptibility to ventricular fibrillation. QT interval dispersion may be less accurate than T-wave alternans in predicting cardiac instability (ventricular fibrillation) but is less affected by mechano-electrical coupling. QT interval dispersion is determined by analyzing ECG signals taken from various electrical sites. One method of determining QT interval dispersion is computing the maximum difference between QT intervals taken across the various electrical sites.

Heart rate variability, which is a measure of autonomic influence, a major factor in triggering cardiac arrhythmias, may be determined by measuring the time between successive R-waves. A time series of successive R—R intervals is formed and a determination is made of the high and low frequency components of heart rate variability. The ratio of the low frequency and the high frequency components is formed indicative of sympathetic activity or vagal withdrawal.

Once it has been established that the risk of the onset of VF is high, a secondary test commences to monitor whether current cardiac activity exceeds a pre-selected range of permissible cardiac activity. The pre-selected is a "running" range such as a sliding average, which is adjusted every cardiac cycle. In this manner, adjustments are made to the range in accordance with monitored cardiac activity normally adjusting to satisfy current physiological need.

Upon detection of cardiac activity exceeding the prescribed acceptable limits of operation, a high amplitude stimulation (pacing) pulse (typically ventricular) is delivered to forestall the development of VF. In this manner the likelihood of VF is severely diminished, if not totally eliminated. The application of the high amplitude pacing pulse may be applied utilizing a number of pacing lead configurations and lead placements. For example, the high amplitude pacing pulse may be applied in the bipolar mode between the tip and ring electrodes of a pacing lead in the right ventricle simultaneously between the tip and ring electrode of a second pacing lead in the great cardiac vein. Simultaneous or offset pacing pulses delivered via unipolar pacing leads to each site, is also within the contemplation of the present invention.

Additionally the invention contemplates providing a far field pacing pulse applied in either ventricle or the great cardiac vein, by shorting together the tip and ring electrodes of the respective leads. The shorted pairs would provide a higher energy pulse since for the same pacing pulse voltage, a higher pulse current results due to the lower resistance of the resulting lower lead impedance. Another lead configuration contemplated by the present invention includes the tip and ring of the coronary sinus pacing lead being shorted together and the high amplitude pacing pulse being delivered between such shorted electrodes and the defibrillation coil of a defibrillation lead located in the right ventricle.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
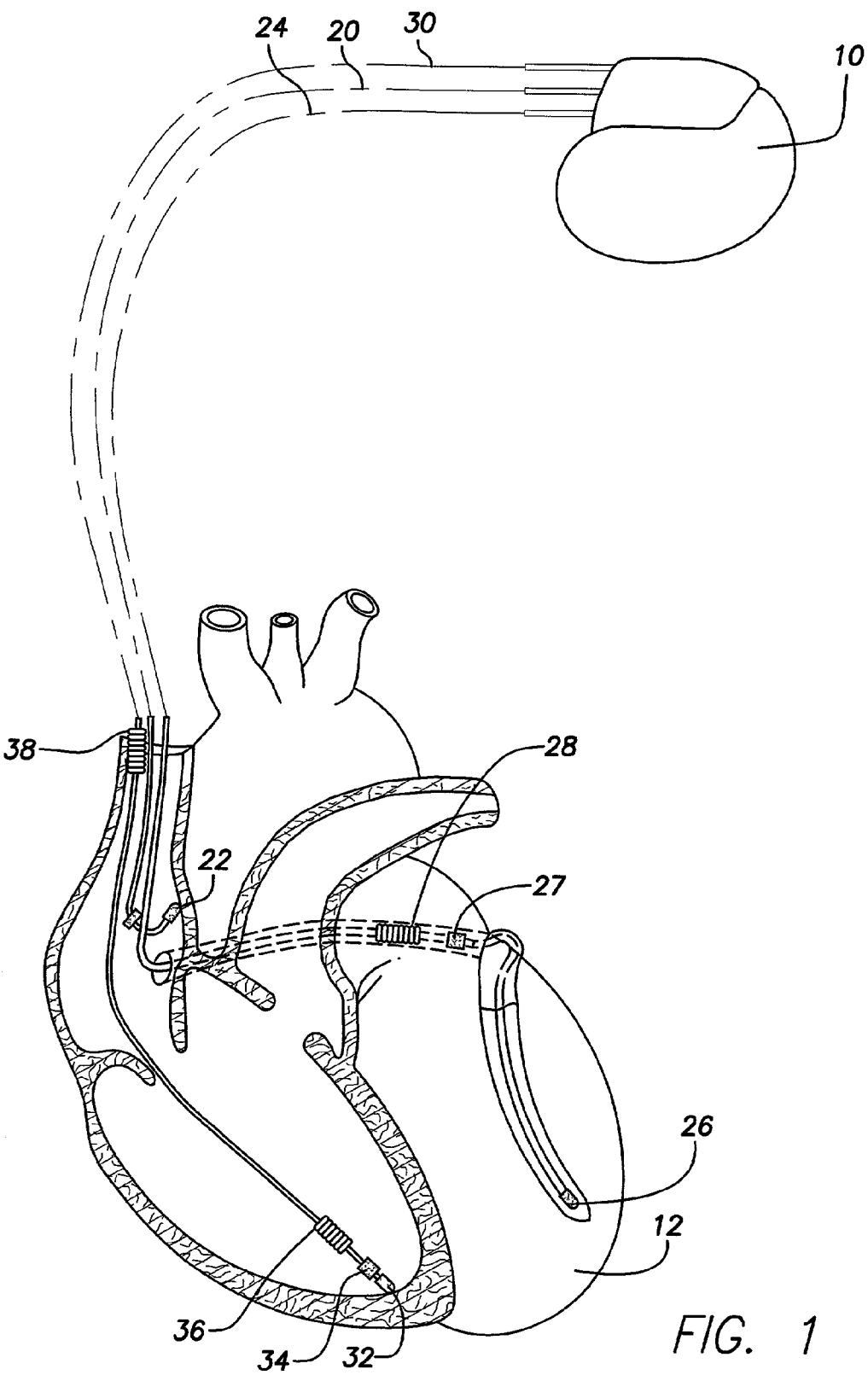
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
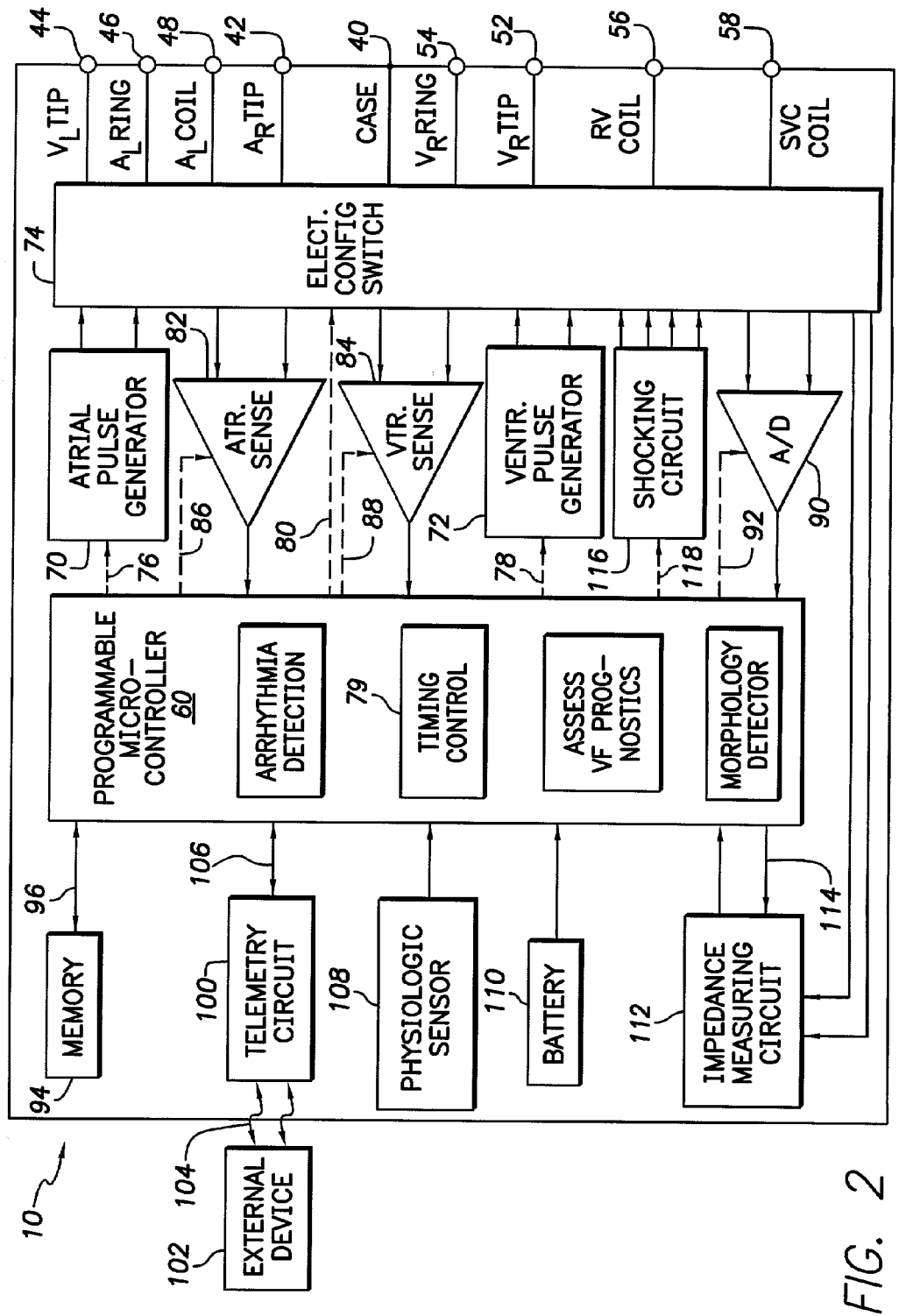
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" that is electrically conductive and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability.

Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves" with the added prefix atrial or ventricular, as the case may be, for clarity) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device. The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 allows intracardiac electrograms and status information relating to the operation of the device 10 (as contained in the microcontroller 60 or memory 94) to be sent to the external device 102 through an established communication link 104.

In the a first embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
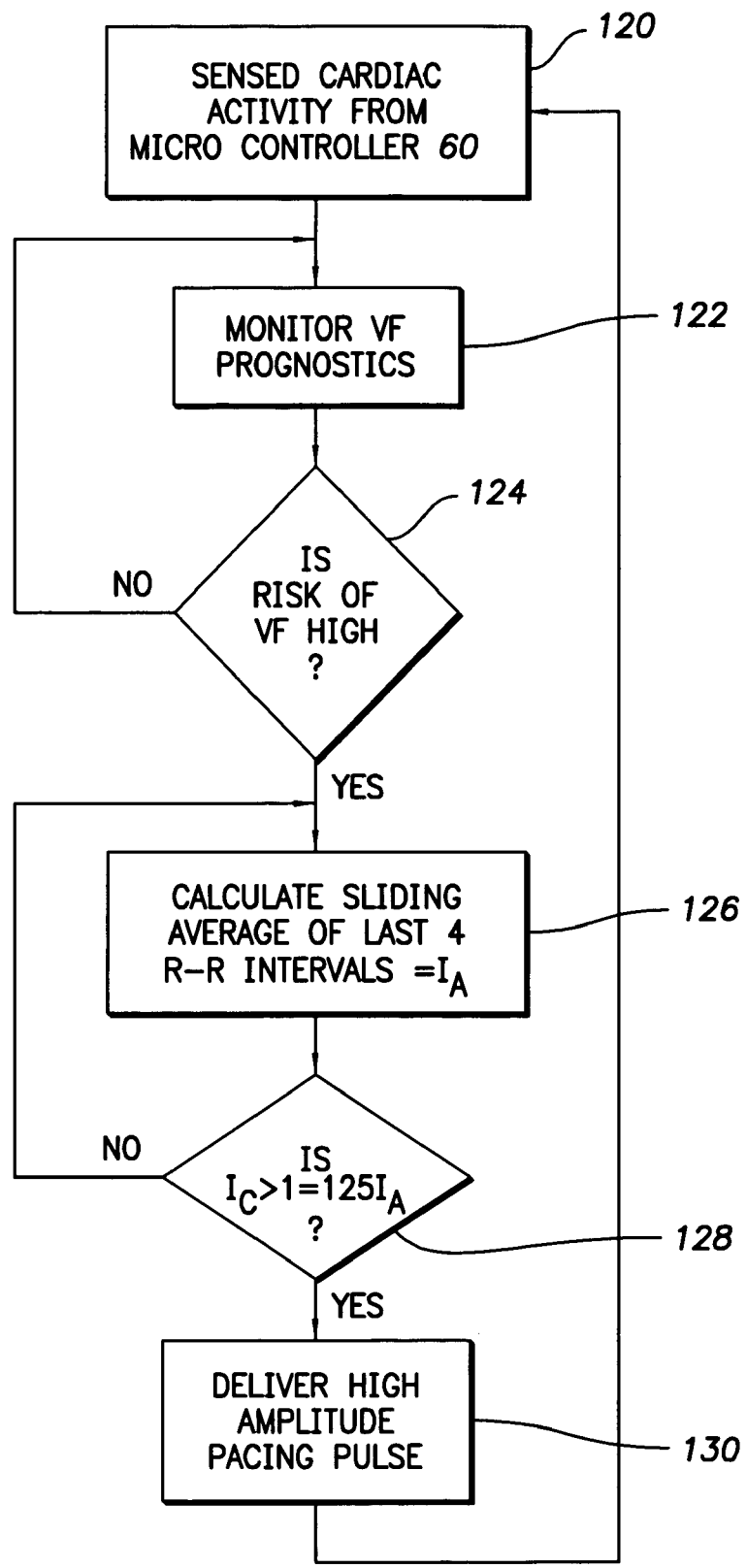
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Simultaneously with other microcontroller functions, sensed cardiac activity is provided by microcontroller 60 in block 120. The sensed cardiac activity signals are analyzed in block 122 to assess VF prognostics. As previously identified, a number of techniques are presently available to undertake such assessment. For example, of the available methods, and without limitation, those taught by Shusterman et al., U.S. Pat. No. 6,308,094, or Street, U.S. Pat. No. 6,115,627 or Sweeney et al., U.S. Pat. No. 6,272,377 are likely candidates for such assessment. Each candidate method or technique provides a basis for establishing whether the value of the examined cardiac parameters presages the onset of an arrhythmia.

In block 124, a determination is made whether the risk of the onset of arrhythmia is high. If the risk is determined to be low, then control is returned to block 122 to continue monitoring VF prognostics. If the risk is determined to be high, the microcontroller 60 commences to calculate a sliding average of past R—R intervals. FIG. 5 of an article entitled "Analysis of the Pattern of Initiation of Sustained Ventricular Arrhythmias in Patients with Implanted Defibrillators" by Eric Taylor M. D. et al. (published in the Journal of Cardiovascular Electrophysiology, Vol. 1, No. 7, July 2000), illustrates an electrogram recording obtained from an ICD showing an initiation sequence of an episode of VF. As observed, there is shown a series of ventricular depolarization's having rather stable intervals of about 520 ms that are labeled with a "Z" followed by a short interval, "Z-Y", followed then by a long Pause "Y-Z". It is observed that two ventricular depolarization's subsequent to the long pause (Y-Z) interval, a tachycardia is initiated, that is, an "A-B" interval followed by a series of "B—B" intervals and then a "B-C" interval. From FIG. 5 of the article, it is also observed that the tachycardia is initiated with a long-coupled ventricular depolarization (L). Of note, a pause is present two cycles before tachycardia onset. It is also observed, that the timing of a PVC follows a long pause in an otherwise normal series of ventricular depolarization's. To forestall such PVC, the invention provides a high amplitude pacing pulse to provoke a heart beat before the late PVC can develop.

In the preferred embodiment, the method used is the measurement of the immediate past R—R intervals. A sliding average of the R—R interval is obtained in block 126 and the next R—R Interval is compared to the sliding average in block 128. If the current R—R interval is less than a predetermined percentage of the sliding average, no action is taken. However, if the current R—R interval exceeds the sliding average by the predetermined amount, the microcontroller 60 causes a high amplitude pacing pulse to be delivered to heart to forestall the occurrence of a PVC. Upon delivery of the high amplitude pacing pulse, control is returned by the microcontroller 60 to sense cardiac signals in block 120 and the VF prognostics are again monitored in block 122. Although a range of values may be used for the predetermined amount such as 10 to 15 percent (%), for the present invention a value of 12.5% is preferable since it provides a good balance between reliability of calculation and a sufficient safety margin to prevent the occurrence of a PVC. Note that in block 128, checking whether the value of the present R—R interval ($I_C$) exceeds the average value of the R—R interval ($I_A$) by greater than 12.5%, is equivalent in mathematical terms to checking whether $I_C > 1.125\, I_A$. For purposes of calculating a sliding average, only the immediate past four values of the R—R interval are used. Subsequent to the test in block 128 the oldest value of the R—R interval is then dropped and the immediate past value of the interval is used to re-calculate the average. In this manner the average "slides" along with the new values of the R—R interval to maintain a current average of the R—R interval. The sliding average therefore represents a statistical indicator or indicia related to a preselected number of the immediate past occurring consecutive R—R intervals.

The sliding average calculated in block 126 requires the average to be recomputed after each R—R interval so as to produce a "current" average, hence the term sliding average, rather than static average. With regards to FIG. 5 of the article, it is noted that the long pause occurring at Y-Z is indicated to be 630 ms a dramatic difference between the normal R—R interval duration of about 520 ms. In the preferred embodiment the four immediate past R—R intervals are used as a benchmark value. However a smaller or larger number may be used in the practice of the invention.

Furthermore, the value of 12.5% is selected as a measure of how much a current R—R interval must exceed the sliding average before the microcontroller 60 triggers the delivery of a high amplitude pacing pulse. Although a percentage greater than 12.5% may be used, such greater percentage may in effect cause the triggering of a high amplitude pacing pulse to be too late. In other words, a PVC may develop before remedial action can be taken. In the preferred embodiment a sliding average of the immediate four past occurring consecutive R—R intervals was described in the calculation of a statistical indicia relating to such intervals. However, other mathematical techniques that may be used in the calculation of a statistical indicia, are also contemplated by the present invention. As mere examples, a median or an exponentially smoothed average of a preselected number of past R—R intervals may be used. The exponential average is a technique that weights the most recent R—R interval to a greater degree than the other immediate past R—R intervals.

Once the microcontroller 60 provides a command to deliver a high amplitude pacing pulse, several lead electrode configurations are selectable to receive the pacing pulse. One configuration utilizes a conventional bipolar lead with the high amplitude pacing pulse delivered across the right ventricular tip electrode 32 and the right ventricular ring electrode 34. As an enhancement, the high amplitude pacing pulse could also be simultaneously applied between a tip and ring electrode of a bipolar lead located in the great cardiac vein (not shown). The high amplitude pacing pulse between the tip and ring electrodes is in the range of about 5 volts up to a maximum of about 10 volts.

Another embodiment includes the use of two bipolar leads arranged in a unipolar configuration for applying the high amplitude pacing pulse to the right ventricular lead where the tip electrode 32 and ring electrode 34 are electrically shorted together and the left ventricular lead where the tip electrode 26 and ring electrode 27 are electrically shorted together. A further embodiment includes application of the high amplitude pacing pulse between the right ventricular coil 36 and the left ventricular lead where the tip electrode 26 and ring electrode 27 are shorted together.

The shorted pairs of electrodes act as larger electrodes and therefore a larger magnitude pulse may be delivered. For the present invention high amplitude pulses in the range of 20 volts is also contemplated. Since the shorted electrodes provide an essentially lower impedance, the same voltage pulse as was applied before the electrodes were shorted together, will provide a higher magnitude pacing current.

The above described configurations, are accomplished by means of electrode configuration switch 74 which establishes the respective electrode configurations in response to specific commands from the microcontroller 60 via control signal 80. Pacing pulses are also directed to the various electrodes by means of switch 74 under the control of microcontroller 60. Furthermore, in terms of stimulation pulse delivery, it is to understood that applying a stimulation pulse between electrode site's is equivalent to having one electrode function as the "load" terminal with the other electrode site functioning as the return terminal.

Although the invention has been described and illustrated with a certain degree of particularity, it is to be understood that those skilled in the art will recognize a variety of applications and appropriate modifications within the spirit of the invention and the scope of the claims.

What is claimed is:

1. A cardiac stimulation device to prevent initiation of ventricular fibrillation (VF), the device comprising:
   a microprocessor;
   a pulse generator coupled to the microprocessor and adapted to deliver stimulation pulses to selected cardiac sites; and
   a sensing circuit electrically coupled to the microprocessor and to selected chambers of the heart and adapted to sense electrical activity in the selected chambers;
   wherein the microprocessor monitors cardiac electrical activity to assess ventricular fibrillation (VF) prognostics predictive of the onset of an arrhythmia of the heart;
   wherein the microprocessor is operative to monitor an occurrence of R-waves and to calculate a statistical indicia related to a plurality of immediate past occurring consecutive R—R intervals;
   wherein if the monitored VF prognostics fall within a prescribed high risk level of cardiac activity, the microprocessor is operative to compare a current R—R interval to the indicia, and to prevent initiation of ventricular fibrillation by triggering the pulse generator to deliver a single high amplitude pacing pulse to at least one cardiac site if the current R—R interval exceeds the indicia by a prescribed amount; and
   wherein the microprocessor is operative to compare a current R—R interval to the indicia to confirm the necessity of delivering the single high amplitude pacing pulse once the monitored VF prognostics fall within a prescribed high risk level of cardiac activity to avoid response to false positives.

2. The cardiac stimulation device of claim 1 wherein the microprocessor calculates a sliding average value of an R—R interval of the immediate past occurring R—R Intervals as the statistical indicia.

3. The cardiac stimulation device of claim 2, wherein the pulse generator Is triggered to deliver the single high amplitude pacing pulse when a current R—R interval exceeds the indicia by a value in the range of about 10 to 15 percent.

4. The cardiac stimulation device of claim 3, wherein the single high amplitude pacing pulse is delivered when a current R—R interval exceeds the indicia by about 12.5 percent.

5. The cardiac stimulation device of claim 1, wherein the single high amplitude pacing pulse is in the range of between about 5 and 10 volts.

6. The cardiac stimulation device of claim 1, further comprising:
   a bipolar pacing lead located in a right ventricle, the bipolar pacing lead having a tip electrode and a ring electrode;
   wherein the microprocessor triggers the pulse generator to deliver the single high amplitude pacing pulse between the tip electrode and the ring electrode of the bipolar pacing lead located in the right ventricle.

7. The cardiac stimulation device of claim 6, further comprising:
   a bipolar pacing lead located in a great cardiac vein, the bipolar pacing lead having a tip electrode and a ring electrode;
   wherein the microprocessor triggers the pulse generator to deliver the single high amplitude pacing pulse between the tip electrode and the ring electrode of the bipolar pacing lead located in the great cardiac vein simultaneously with the delivery of the single high amplitude pacing pulse to the right ventricle.

8. The cardiac stimulation device of claim 1, further comprising:
   a bipolar pacing lead located in a right ventricle, the bipolar pacing lead having a tip electrode and a ring electrode; and
   a bipolar pacing lead located in a coronary sinus, the bipolar pacing lead having a tip electrode and a ring electrode;
   wherein the microprocessor triggers the pulse generator to deliver the single high amplitude pacing pulse to electrically shorted together tip and ring electrodes of the bipolar pacing lead located in the right ventricle simultaneously with the delivery of the single high amplitude pacing pulse to electrically shorted together tip and ring electrodes of the bipolar lead located in the coronary sinus.

9. The cardiac stimulation device of claim 1, further comprising:
a bipolar pacing lead located in a right ventricle, the bipolar pacing lead having a tip electrode and a ring electrode; and
a bipolar pacing lead located in a left ventricle, the bipolar pacing lead having a tip electrode and a ring electrode:
wherein the microprocessor triggers the pulse generator to deliver the single high amplitude pacing pulse to electrically shorted together tip and ring electrodes of the bipolar pacing lead located in the right ventricle simultaneously with the delivery of the single high amplitude pacing pulse to electrically shorted together tip and ring electrodes of the bipolar lead located in the left ventricle.

10. The cardiac stimulation device of claim 1, further comprising:
a bipolar pacing lead located in a coronary sinus, the bipolar pacing lead having a tip electrode and a ring electrode; and
a defibrillation lead located in a right ventricle, the defibrillation lead having a coil electrode;
wherein the microprocessor triggers the pulse generator to deliver the single high amplitude pacing pulse to electrically shorted together tip and ring electrodes of the bipolar pacing lead located in the coronary sinus simultaneously with the delivery of the single high amplitude pacing pulse to the coil electrode of the defibrillation lead located in the right ventricle.

11. The cardiac stimulation device of claim 1, further comprising:
a defibrillation lead located in a right ventricle, the defibrillation lead having a coil electrode; and
wherein the device is contained within an electrically conductive can, and wherein the microprocessor triggers the pulse generator to deliver the single high amplitude pacing pulse between a coil electrode of a defibrillation lead located in the right ventricle and the can.

12. The cardiac stimulation device of claim 1 wherein the monitored VF prognostics comprises at least one of ventricular tachycardia duration, ventricular tachycardia rate, and widening of QRS complex.

13. A method of preventing an initiation of ventricular fibrillation (VF), the method comprising:
monitoring VF prognostics predictive of an onset of an arrhythmia of the heart;
calculating a statistical indicia related to a predetermined number of immediate past consecutive R—R intervals;
determining whether the VF prognostics fall within a prescribed high risk level of cardiac activity;
monitoring a current value of the R—R interval when the VF prognostics fall within the prescribed high risk level of cardiac activity;
delivering a single high amplitude cardiac pacing pulse to at least one preselected cardiac site when the current R—R interval exceeds the indicia by a predetermined amount to prevent initiation of ventricular fibrillation.

14. The method of claim 13 comprising calculating a sliding average of a predetermined number of the immediate past consecutive R—R intervals as the statistical indicia.

15. The method of claim 14 comprising calculating a sliding average value of an R—R interval of immediate past four consecutive R—R intervals.

16. The method of claim 13 wherein the single high amplitude pacing pulse has a magnitude in the range of about 5 to 20 volts.

17. The method of claim 13 comprising delivering the single high amplitude pacing pulse between a tip electrode and a ring electrode of a bipolar lead located in the right ventricle.

18. The method of claim 17 further comprising delivering the single high amplitude pacing pulse between a tip electrode and a ring electrode of a bipolar pacing lead located in the great cardiac vein simultaneously with the delivery of the single high amplitude pacing pulse to the right ventricle.

19. The method of claim 13 comprising delivering the single high amplitude pacing pulse to electrically shorted together tip and ring electrodes of a bipolar pacing lead located in the right ventricle simultaneously with the delivery of the single high amplitude pacing pulse to electrically shorted together tip and ring electrodes of a bipolar lead located in the coronary sinus.

20. The method of claim 13 comprising delivering the single high amplitude pacing pulse to electrically shorted together tip and ring electrodes of a bipolar pacing lead located in the right ventricle simultaneously with the delivery of the single high amplitude pacing pulse to electrically shorted together tip and ring electrodes of a bipolar lead located in the left ventricle.

21. The method of claim 13 comprising delivering the single high amplitude pacing pulse to electrically shorted together tip and ring electrodes of a bipolar pacing lead located in the coronary sinus simultaneously with the delivery of the single high amplitude pacing pulse to a coil electrode of a defibrillation lead located in the right ventricle.

22. The method of claim 13, wherein the method is undertaken by an implantable cardiac stimulation device having an electrically conductive can, comprising delivering the high amplitude pacing pulse between a coil electrode of a defibrillation lead located in the right ventricle and the can.

23. The method of claim 13 wherein the monitoring VF prognostics comprises at least one of ventricular tachycardia duration, ventricular tachycardia rate, and widening of QRS complex.

24. A cardiac stimulation device for pacing a patient to prevent ventricular fibrillation comprising:
means for monitoring cardiac electrical activity in selected chambers of the heart;
stimulation means for delivering electrical stimulation to selected cardiac sites;
means for calculating an indicia representative of prior cardiac activity;
means for determining a potential of an onset of ventricular fibrillation based upon the monitored cardiac activity;
means for monitoring current cardiac activity when the potential of the onset of ventricular fibrillation exceeds a pre-selected value;
wherein the monitoring means comprises means for monitoring selected ventricular fibrillation prognostics;
wherein the monitoring means further monitors the occurrence of R-waves and the calculating means calculates a sliding average value of an R—R interval of a preselected number of immediate past occurring consecutive R—R intervals as an indicia of prior cardiac activity; and
means for controlling the stimulation means to deliver a single high magnitude pacing pulse to a selected cardiac site when a current cardiac activity exceeds the indicia by a predetermined amount.

25. The cardiac stimulation device of claim 24 comprising comparison means for comparing a current R—R interval to the indicia and wherein the stimulation means delivers the single high magnitude pacing pulse to selected cardiac sites when the current R—R interval exceeds the indicia by a predetermined amount.

26. The cardiac stimulation device of claim 25 wherein the stimulation means delivers the single high magnitude pacing pulse to the selected cardiac site when a current R—R interval exceeds the indicia by an amount in the range of about 12.5 percent.

27. The cardiac stimulation device of claim 25 wherein the stimulation means delivers the single high magnitude pacing pulse to the selected cardiac site when a current R—R interval exceeds the indicia by an amount in the range of about 10 to 15 percent.

28. The cardiac stimulation device of claim 24 wherein the stimulation means delivers the single high magnitude pacing pulse in the range of between 5 to 20 volts.

29. The cardiac stimulation device of claim 24 comprising means for delivering the single high magnitude pacing pulse between a tip electrode and a ring electrode of a bipolar lead located in a right ventricle.

30. The cardiac stimulation device of claim 24 comprising means for delivering the single high magnitude pacing pulse between a tip electrode and a ring electrode of a bipolar pacing lead located in a great cardiac vein simultaneously with the delivery of the single high magnitude pacing pulse to a right ventricle.

31. The cardiac stimulation device of claim 24 comprising means for delivering the single high magnitude pacing pulse to electrically shorted together tip and ring electrodes of a bipolar pacing lead located in a right ventricle simultaneously with the delivery of the single high magnitude pacing pulse to electrically shorted together tip and ring electrodes of a bipolar lead located in a coronary sinus.

32. The cardiac stimulation device of claim 24 comprising means for delivering the single high magnitude pacing pulse to electrically shorted together tip and ring electrodes of a bipolar pacing lead located in a right ventricle simultaneously with the delivery of the single high magnitude pacing pulse to electrically shorted together tip and ring electrodes of a bipolar lead located in a left ventricle.

33. The cardiac stimulation device of claim 24 comprising means for delivering the single high magnitude pacing pulse to electrically shorted together tip and ring electrodes of a bipolar pacing lead located in a coronary sinus simultaneously with the delivery of the single high magnitude pacing pulse to a coil electrode of a defibrillation lead located in a right ventricle.

34. The cardiac stimulation device of claim 24 comprising means for containing the cardiac stimulation device in an electrically conductive can, the device further comprising means for delivering the single high magnitude pacing pulse between a coil electrode of a defibrillation lead located in a right ventricle and the can.

35. The cardiac stimulation device of claim 24 wherein the means for determining a potential of an onset of ventricular fibrillation comprises at least one of ventricular tachycardia duration, ventricular tachycardia rate, and widening of QRS complex.

36. A cardiac stimulation device comprising:
a microprocessor;
a pulse generator coupled to the microprocessor and adapted to deliver stimulation pulses to selected cardiac sites; and
a sensing circuit electrically coupled to the microprocessor and selected chambers of the heart and adapted to sense electrical activity in the selected chambers and wherein the microprocessor monitors an occurrence of R-waves corresponding to the electrical activity and calculates a statistical indicia related to a preselected number of immediate past occurring consecutive R—R intervals and wherein the microprocessor monitors cardiac electrical activity to assess ventricular fibrillation (VF) prognostics predictive of an onset of VF of the heart, wherein if the monitored VF prognostics fall within a prescribed high risk range of cardiac activity, the microprocessor is operative to compare a current R—R interval to the indicia, and to trigger the pulse generator to deliver a single high amplitude pacing pulse to at least one cardiac site if the current R—R interval exceeds the indicia by a prescribed amount to prevent initiation of VF.

37. The stimulation device of claim 36 wherein the indicia is the average value of an R—R interval of the preselected number of the immediate past occurring R—R intervals.

38. The stimulation device of claim 37 wherein the preselected number is four.

* * * * *